United States Patent [19]

Grau

[11] Patent Number: 4,701,440

[45] Date of Patent: Oct. 20, 1987

[54] INSULIN DERIVATIVES, PROCESSES FOR THEIR PREPARATION AND THEIR USE, AND PHARMACEUTICAL AGENTS FOR THE TREATMENT OF DIABETES MELLITUS

[75] Inventor: Ulrich Grau, Hofheim am Taunus, Fed. Rep. of Germany

[73] Assignee: Hoechst Aktiengesellschaft, Fed. Rep. of Germany

[21] Appl. No.: 873,456

[22] Filed: Jun. 6, 1986

Related U.S. Application Data

[63] Continuation of Ser. No. 632,845, Jul. 30, 1984, abandoned.

[30] Foreign Application Priority Data

Jul. 22, 1983 [DE] Fed. Rep. of Germany ........ 3326472

[51] Int. Cl.$^4$ .................. A61K 37/26; C07K 7/40
[52] U.S. Cl. .......................... 514/3; 514/4; 530/303
[58] Field of Search .................. 530/303; 514/3, 4

[56] References Cited

FOREIGN PATENT DOCUMENTS 0092280  10/1983  European Pat. Off. .
0118546  7/1982   Japan .................. 260/112.7

OTHER PUBLICATIONS

Reprint from Excerpta Internation Congress Series No. 231 "Proceedings of the VII Congress of the International Diabetes Federation", Buenos Aires, Aug. 23–28, 1970.

Primary Examiner—Frederick E. Waddell
Attorney, Agent, or Firm—Finnegan, Henderson, Farabow, Garrett & Dunner

[57] ABSTRACT

The invention relates to insulin derivatives of the formula I

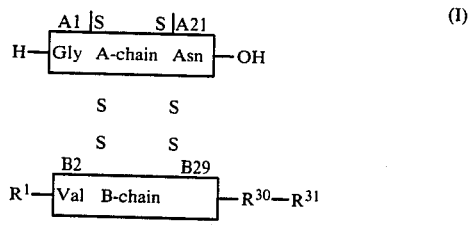

in which $R^1$ denotes H or H—Phe, $R^{30}$ represents the radical of a neutral L-aminoacid and $R^{31}$ represents a physiologically acceptable organic group of basic character with up to 50 carbon atoms, these derivatives having an isoelectric point between 5.8 and 8.5, processes for their preparation and their use, and agents containing these derivatives for the treatment of diabetes mellitus.

21 Claims, No Drawings

INSULIN DERIVATIVES, PROCESSES FOR THEIR PREPARATION AND THEIR USE, AND PHARMACEUTICAL AGENTS FOR THE TREATMENT OF DIABETES MELLITUS

This application is a continuation of application Ser. No. 632,845, filed July 30, 1984, now abandoned.

At present, in general, formulations of the hypoglycemic hormone insulin are administered parenterally in the therapy of diabetes millitus. The particular nature of insulin and its metabolism mean that the duration of action of a simple solution is only very short, i.e. for lasting control of the blood sugar in diabetics, it is necessary to administer either a continuous infusion with metering instruments, several daily injections or a delayed-action insulin formulation. Those states of insulin which are sparingly soluble at the injection site (for example crystalline or amorphous states) are of particular importance here as delayed action principles. Zinc insulin crystals or protamine insulin crystals, which release insulin over a certain period of time during their slow redissolving process, are further examples to be considered.

It has now proved to be extremely helpful in the therapy to have available various insulin products of which the action characteristics fulfill as closely as possible the requirements of the individual patient. In connection with non-optimum adjustment, delayed complications of diabetes, including retinopathy, neuropathy, nephropathy and micro- and macro-angiopathy, are discussed in particular, besides the immediate effects, such as hyper- or hypo-glycemia.

The insulin deficiency in a diabetic means that the body can no longer achieve its natural hormonal equilibrium.

The object of the invention is to provide an insulin derivative or a corresponding pharmaceutical agent with which the natural hormonal equilibrium can be better approximated in a diabetic condition and with which this equilibrium can be better maintained than by administration of insulin in the forms hitherto customary.

According to the invention, this object is now achieved by one or more insulin derivative(s), the B chain of which carries on organic group of basic character in the C-terminal region, and by a pharmaceutical agent which contains this insulin derivative as the active compound.

Insulin derivatives which carry Arg—OH or Arg—Arg—OH radicals on the C-terminal end of the B chain have already been described. As is known, these derivatives are formed as natural intermediates on enzymatic conversion of proinsulin into insulin in vivo, and small amounts can also be detected in pancreas extracts. The radicals mentioned are usually split off by trypsin and/or carboxypeptidase B or enzymes having a similar specificity, and the unmodified insulin being liberated.

The invention relates to insulin derivatives of the formula I,

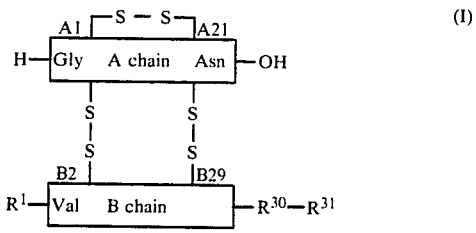

in which $R^1$ denotes H or H—Phe, $R^{30}$ represents the radical of a neutral L-aminoacid which can be genetically coded and $R^{31}$ represents a physiologically acceptable organic group of basic character having up to 50 carbon atoms, in the build-up of which 0 to 3 α-aminoacids participate and in which the optional terminal carboxyl group can be present in the free form, as an ester function, as an amide function, as a lactone or reduced to $CH_2OH$, and wherein, if $R^1$ represents H—Phe, the C-terminus —$R^{30}$—$R^{31}$ cannot denote —Thr—(Arg)$_m$—OH, —Ala—(Arg)$_m$—OH or —Ser—(Arg)$_m$—OH, where m is 1 or 2, which have an isoelectric point between 5.8 and 8.5, and to physiologically acceptable salts thereof.

$R^{31}$ is understood as meaning, in particular, a radical of the formula —$X_n S$, in which n is 0, 1, 2 or 3, X represents identical or different radicals of naturally occurring neutral or basic L-aminoacids, preferably basic L-aminoacids, in particular Arg, Lys, His or Orn and/or of the D-aminoacids corresponding to these, and S denotes OH or a physiologically acceptable group which blocks the carboxyl group and which, if n is 0, carries a positively charged or protonatable basic radical or, if n>0, can carry such a radical, and in which the C-terminus —X—S can also represent the radical of an aminoacid reduced to the corresponding alcohol or, if n is 2 or 3, can represent the homoserinelactone radical.

Preferred insulin derivatives of the formula I are those in which $R^{30}$ represents the radical of a neutral L-aminoacid which can be genetically coded, (a)

$R^1$ denotes H and $R^{31}$ (a 1) denotes a physiologically acceptable group $S^B$ which blocks the carboxyl group and carries a positively charged or protonatable basic radical, (a 2.1) represents $X^N$—$S^B$, in which $X^N$ denotes the radical of a naturally occurring neutral L-aminoacid or the D-form thereof, (a 2.2) represents $X^B$—S, in which $X^B$ denotes the radical of a naturally occurring basic L-aminoacid or the D-form thereof and S denotes OH or a group which blocks the carboxyl group and optionally carries a positively charged or protonatable basic radical, (a 2.3) represents the radical Y of a basic aminoacid $X^B$ reduced to the corresponding alcohol, (a 3.1) represents —$X_n$—S, in which n is 2 or 3, X denotes the radicals $X^N$ and/or $X^B$ and, if all the radicals X are $X^N$, S can denote only $S^B$, (a 3.2) represents —$X_n$—Y, in which n is 1 or 2, (a 3.3) represents —$X^B$—Z, —$X^B$—$X^N$—Z, —$X^N$—$X^B$—Z or —$X^B$—$X^B$—Z, in which Z is Y or denotes the homoserine-lactone radical, or (b)

$R^1$ denotes H-Phe and $R^{31}$ (b 1) is as defined under (a 1), (b 2.1) is as defined under (a 2.1), (b 2.2) denotes Lys—OH, D—Lys—OH, D—Arg—OH, Hyl—OH, D—Hyl—OH, Orn—OH, D—Orn—OH, Cit—OH, D—Cit—OH, His—OH or D—His—OH, (b 2.3) represents $X^B$—S', in which S' has the meaning of S, with the exception of OH, (b 2.4) is as defined under (a 2.3), (b 3.1) represents —X—X'—OH or —X'—X—OH, in which X' is as defined under (b 2.2), (b 3.2) represents $X_2$—S', (b 3.3) is as defined under (a 3.1), in which n is 3, (b 3.4) is as defined under (a 3.2) or (a 3.3).

Insulin derivatives which carry phenylalanine in positions B1 are particularly preferred. Those which contain Ala, Thr or Ser in position B30 are also preferred.

The A chain and the (B2-29) chain of the compounds according to the invention advantageously have the sequence of bovine or porcine insulin, but in particular that of human insulin.

The aminoacid radicals X, $X^N$ and $X_B$ and the radicals Y and Z can independently of one another be in the D- or L-configuration. However, the L-configuration is preferred for all these radicals.

The following L-aminoacids can be genetically coded: Gly, Ala, Ser, Thr, Val, Leu, Ile, Asp, Asn, Glu, Gln, Cys, Met, Arg, Lys, His, Tyr, Phe, Trp and Pro (neutral aminoacids are underlined).

A neutral, naturally occurring aminoacid is understood as meaning, in particular, Gly, Ala, Ser, Thr, Val, Leu, Ile, Asn, Gln, Cys, Met, Tyr, Phe, Pro and Hyp. A basic, naturally occurring aminoacid is understood as meaning, in particular, Arg, Lys, Hyl, Orn, Cit or His.

Groups which may block a free carboxyl function on the C-terminal end of the B chain in the compounds according to the invention are understood as meaning, above all, ester and amide groups, preferably ($C_1$ to $C_6$)-alkoxy, ($C_3$ to $C_6$)-cycloalkoxy, $NH_2$, ($C_1$ to $C_6$)-alkyl-amino, di-($C_1$ to $C_6$)-alkylamino or basic groups, such as amino-($C_2$ to $C_6$)-alkoxy, ($C_1$ to $C_4$)-alkylamino-($C_2$ to $C_6$)-alkoxy, di-($C_1$ to $C_4$)-alkylamino-($C_2$ to $C_6$)-alkoxy, tri-($C_1$ to $C_4$)-ammonio-($C_2$ to $C_6$)-alkoxy, amino-($C_2$ to $C_6$)-alkylamino, [($C_1$ to $C_4$)-alkylamino]-($C_2$ to $C_6$)-alkyl amino, [di-($C_1$-$C_4$)-alkylamino]-($C_2$ to $C_6$)-alkylamino or [tri-($C_1$ to $C_4$)-alkylammonio]-($C_2$ to $C_6$)-alkylamino, in particular —O—$[CH_2]_p$—$NR_2$, —O—$[CH_2]_p$—$N^{\oplus}R_3$, —NH—$[CH_2]_p$—$NR_2$ or —NH—$[CH_2]_p$—$N^{\oplus}R_3$, in which p is 2 to 6 and the radicals R are identical or different and represent hydrogen or ($C_1$ to $C_4$)-alkyl.

In the series of insulin derivatives according to the invention, the following compounds may be mentioned as examples, without limiting the invention to these:

Des-Phe$^{B1}$-porcine insulin-Arg$^{B31}$-OH
Des-Phe$^{B1}$-human insulin-Arg$^{B31}$-OH
Des-Phe$^{B1}$-porcine insulin-Arg$^{B31}$-Arg$^{B32}$-OH
Des-Phe$^{B1}$-human insulin-Arg$^{B31}$-Arg$^{B32}$-OH
Porcine insulin-Arg$^{B31}$-OCH$_3$
Human insulin-Arg$^{B31}$-OCH$_3$
Bovine insulin-Arg$^{B31}$-OCH$_3$
Porcine insulin-Arg$^{B31}$-Arg$^{B32}$-OCH$_3$
Human insulin-Arg$^{B31}$-Arg$^{B32}$-OCH$_3$
Des-Thr$^{B30}$-human insulin-Val$^{B30}$-Arg$^{B31}$-OH
Des-Thr$^{B30}$-human insulin-Val$^{B30}$-Ala$^{B31}$-Arg$^{B32}$-OH
Human insulin-Lys$^{B31}$-OH
Human insulin-D-Arg$^{B31}$-OH
Human insulin-D-Arg$^{B31}$-Arg$^{B32}$-OH
Human insulin-Arg$^{B31}$-D-Arg$^{B32}$-OH
Human insulin-Lys$^{B31}$-Arg$^{B32}$-OH
Human insulin-Arg$^{B31}$-Lys$^{B32}$-OH
Human insulin-Argininol$^{B31}$
Human insulin-Val$^{B31}$-Arg$^{B32}$-OH
Human insulin-Val$^{B31}$-Arg$^{B32}$-Arg$^{B33}$-OH
Human insulin-Arg$^{B31}$-Argininol$^{B32}$
Human insulin-Lys$^{B31}$-Arg$^{B32}$-Arg$^{B33}$-OH

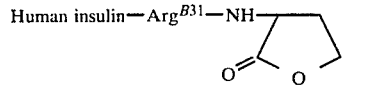

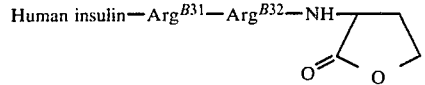

Human insulin-Arg$^{B31}$-NH$_2$
Human insulin-Arg$^{B31}$-Arg$^{B32}$-NH$_2$
Human insulin-Orn$^{B31}$-OH
Human insulin-Leu$^{B31}$-Cit$^{B32}$-OH
Human insulin-(B30)-OCH$_2$CH$_2$-NH$_2$
Human insulin-(B30)-NH-CH$_2$CH$_2$-NH$_2$
Human insulin-Arg$^{B31}$-O-CH$_2$-CH$_2$-NH$_2$
Human insulin-Arg$^{B31}$-CH$_2$-CH$_2$-N(CH$_3$)$_2$
Human insulin-(B30)-O-CH$_2$-CH$_2$-N$^{\oplus}$(CH$_3$)$_3$
Human insulin-(B30)-NH-CH$_2$-CH$_2$-N$^{\oplus}$(CH$_3$)$_3$
Human insulin-Leu$^{B31}$-O-CH$_2$-CH$_2$-CH$_2$-N$^{\oplus}$(C$_2$H$_5$)$_3$
Human insulin-Trp$^{B31}$-Trp$^{B32}$-Trp$^{B33}$-NH(CH$_2$)$_6$-N$^{\oplus}$[(CH$_2$)$_3$CH$_3$]$_3$ The invention also relates to a process for the preparation of insulin derivatives of the formula I, which comprises (a) condensing a des-octapeptide (B23-30)-insulin of the formula II

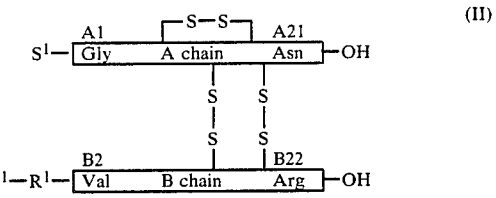

(II)

in which $R^1$ denotes Phe or a bond and $S^1$ denotes an amino-protective group which can be split off by proton solvolysis or by β-elimination, such as the tert.-butoxy-carbonyl (Boc), the tert.-amyloxycarbonyl (Aoc) or the methylsulfonylethoxycarbonyl (Msc) radical, with a peptide of the formula III

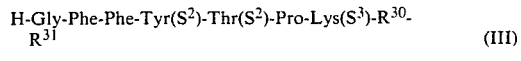

(III)

in which $R^{30}$ and $R^{31}$ have the meanings defined above, $S^2$ represents hydrogen, Bzl or Bu$^t$ and $S^3$ represents a urethane-protective group, such as Boc, Moc, Fmoc or Z, it being possible, if necessary, for free COOH, OH, SH, NH$^2$, guanidino and/or imidazole groups present in the radicals $R^{30}$ and $R^{31}$ to be protected in a manner which is known per se, and, if appropriate, splitting off the protective groups present in a manner which is known per se, (b) reacting, in the presence of trypsin or a trypsin-like endopeptidase, a des-B30-insulin of the formula I in which $R^1$ represents H or H—Phe and the C-terminus $R^{30}$-$R^{31}$ together represents OH, with a compound of the formula IV

　　　(IV)

in which $R^{30}$ and $R^{31}$ have the meanings defined above and free COOH, OH, SH, $\omega$—NH$_2$, guanidino and/or imidazole functions present are, if necessary, protected in a manner which is known per se, and then, if appropriate, splitting off the protective groups present in a manner which is known per se, or (c) for the preparation of an insulin derivative with aminoacid radicals in the L-configuration in $R^{31}$, chemically and/or enzymatically splitting a proinsulin, proinsulin analog or preproinsulin analog or an intermediate of these compounds.

In process variant (a), for example, the N$\alpha^{A1}$, N$\alpha^{B1}$-bis-Boc derivative of a des-octapeptide-(B23-30)-insulin is reacted directly with one equivalent of a compound of the formula III by a procedure analogous to that described in U.S. Pat. No. 4,029,642, slightly less than the equivalent amount of dicyclohexylcarbodiimide being used as the condensing agent, in the presence of 1-hydroxybenzotriazole.

Since it is usually not necessary to protect the carboxyl groups in this process variant, damage to the insulin derivative is usually also avoided both during the esterification and during the alkaline hydrolysis. Unreacted des-octapeptide and a peptide formed by condensation of IV with Asp$^{A21}$-OH can easily be removed, on the basis of their different molecular size and charge number, by partition chromatography on Sephadex ®-LH 20 or by gel chromatography on Sephadex ®-G 75 or G 50 super-fine.

To split off the tert.-butyl protective groups, it is only necessary to treat the reaction product with trifluoroacetic acid at room temperature for 30–60 minutes. This reaction does not damage the insulin derivative. If the methylsulfonylethoxycarbonyl radical is chosen as the N-protective group, treatment with an alkali for removal by $\beta$-elimination is necessary. The reaction conditions are such that (for example 0.1N NaOH, 0° C., 5 seconds) the insulin derivative is not damaged. The N$\alpha^{A1}$, N$\alpha^{B1}$-bis-Boc-des-B$_{23-30}$-octapeptide-insulin from pigs used as the starting substance is prepared, for example, by the following route:

Porcine insulin is reacted with excess tert.-butoxycarbonyl-N-hydroxysuccinimide ester in a mixture of dimethylformamide, dimethylsulfoxide and water in the presence of N-ethylmorpholine. The N$\alpha$hu A1, N$\alpha^{B1}$, N$\epsilon^{B29}$-tris-Boc-insulin to be expected is thereby formed.

Small portions of trypsin are now added to a solution of this compound in dimethylformamide and tris buffer (pH 7.5) until no further starting substance can be found by electrophoresis. The N$\alpha^{A1}$, N$\alpha^{B1}$-bis-Boc-des-B$_{23-30}$- octapeptide-insulin is purified by partition chromatography on Sephadex ®-LH 20.

This compound is now reacted with one mole of the peptide of the formula III, which is prepared in a manner which is known per se by the methods of peptide chemistry, 1–2 moles of 1-hydroxybenzotriazole and about 0.9 mole of dicyclohexylcarbodiimide in dimethylformamide at about pH 7–8 (cf. Chem. Ber. 103 (1970), page 788).

The crude product is purified by partition chromatography and freed from the protective groups by treatment with trifluoroacetic acid/anisole at room temperature. After precipitation with ether, isoelectric precipitation from water and chromatography on Sephadex ®-G 75 or G 50 superfine, the compound is electrophoretically pure and can be crystallized in a known manner. The insulin derivative thus obtained is biologically fully active.

Des-Phe$^{B1}$-insulins as starting compounds for the processes according to the invention are known, for example, from German Pat. No. 2,005,658 or European Pat. No. A-46,979.

The des-B30-insulins used as starting compounds in process variant (b) are known, for example, from European Pat. No. A-46,979 or Hoppe-Seyler's Z. Physiol. Chem. 359 (1978) 799. The starting material of the formula IV used in variant (b) is prepared in a manner which is known per se by the methods of peptide chemistry. Protective groups which can be used for IV are described in detail in M. Bodanzyky et al., Peptide Synthesis, Ind. Ed. 1976, Wiley & Sons.

The des-B30-insulin and the compound of the formula IV are condensed with one another by a procedure analogous to that described in U.S. Pat. No. 4,320,196, in the presence of trypsin or a trypsin-like endopeptidase in an organic-aqueous solvent system at pH 5–9 and at a temperature of 20° to 40° C. The resulting insulin derivative can be isolated by the customary methods of peptide chemistry.

Proinsulin from humans or primates is meanwhile accessible by genetic engineering methods as the starting material for process variant (c). The derivatives Arg(B31) and di-Arg(B31-32) are accessible therefrom by simple digestion with trypsin or trypsin-like enzymes. In addition, however, it is also possible to construct relatively simple plasmids which, by splitting of corresponding preproinsulin derivatives, lead to novel insulin derivatives because, instead of the arginine which naturally occurs at B31 or B32, they code other neutral or basic aminoacids.

The preparation of proinsulin using recombinant DNA methodology requires the formation of a DNA sequence which codes the aminoacid sequence of a proinsulin, which can be achieved either by isolation or construction or by a combination of both. The proinsulin DNA is then inserted in a suitable cloning and expression carrier in the reading phase. The carrier serves to transform a suitable microorganism, and the transformed microorganism thereby obtained is then subjected to fermentation conditions, which led to the formation of further copies of the vector containing the proinsulin gene and to the expression of proinsulin, a proinsulin derivative or a proinsulin precursor (or a preproinsulin derivative).

If the expression product is a proinsulin precursor, such a product in general contains the proinsulin aminoacid sequence which, at its terminal amino group, is bonded to a fragment of a protein which is usually expressed by the gene sequence in which the proinsulin or proinsulin derivative has been inserted. The proinsulin aminoacid sequence is bonded to the protein fragment via a site which can be split specifically, which is, for example, methionine. The resulting proinsulin aminoacid sequence is split off from the fused gene product, for example as described in German Pat. No. A-3,232,036, and, after purification, the proinsulin is isolated.

Enzymatic splitting of the proinsulin or proinsulin derivative obtained in this manner is carried out by a procedure analogous to that described in Excerpta Medica International Congress Series No. 231, page 292 et seq. or that described in German Patent Application P 32 09 184 (HOE 82/F 047).

In addition to the known arginine (B30) and diarginine (B31-32) derivatives and those derivatives which are accessible by genetic engineering methods and carry naturally occurring L-aminoacids in $R^{31}$, a number of novel insulin derivatives which exhibit, as a characteristic, one or several basic groups and/or the absence of the free carboxyl group, so that the net charge of the molecule is increased by at least one positive charge in comparison with unmodified insulin or in comparison with des-Phe$^{B1}$-insulin, are accessible with the aid of the semi-synthetic processes described.

These derivatives include, for example, derivatives which, instead of the naturally occurring aminoacids L-Lysine, L-histidine or L-arginine at position B31, contain their D-enantiomers or the usual D- or L-aminoacid analogs which carry a basic grouping (for example ornithine or hydroxylysine) in the side chain. Instead of an aminoacid, the choline ester group, for example, may occur at the site of position B31, in which case two net positive charges are obtained. The aminoacid or the aminoacid analog at position B31 can have a free carboxyl end or can be esterified with simple alcohols (for example methanol or ethanol) or amidated with simple nitrogen bases (for example ammonia or mono- or di-methylamine); in addition, it can be esterified, for example, with choline. A neutral or another naturally occurring basic aminoacid or one of the aminoacid derivatives described above, for example, can follow at position B32; in an analogous manner, the carboxyl group thereof can be free or esterified or amidated. In this case also, the choline ester group or another neutral or basic aminoacid or an aminoacid analog, for example, can follow.

All these insulin derivations have the common characteristic that the additional positive charge(s) on the surface of the molecule gives the molecule an isoelectric point which is shifted into the neutral range. Depending on the derivative, isoelectric points of 5.8 to 8.5, in particular 6.2 to 8.2, are measured in isoelectric focusing. The derivatives in the neutral range are thus less soluble than unmodified insulin or proinsulin, which have their isoelectric point and hence the region of maximum insolubility at pH 5.4, whilst they are usually in dissolved form in the neutral range.

The solubility properties of insulin and proinsulin can be influenced in the region above the isoelectric point, i.e. in the neutral range which is of particular therapeutic interest, by addition of zinc ions. Zinc acts here as a depot principle by stabilizing the hexameric state of the insulin and its tendency towards crystallization. These aggregates dissolve again in the subcutaneous tissue.

Another current depot principle is crystallization of the insulin or proinsulin as a complex with a basic protein, for example globin or protamine.

If proinsulin is used in solution or in association with one of the depot principles described, further proteolytic degradation is required in order to release unmodified, fully active insulin. Intact proinsulin has only about 1/8th of the biological activity of insulin, because, according to theory, some of the bologically active region on the surface, the receptor-binding region, is masked by the C-peptide present in the proinsulin. Needless to say, only homologous proinsulin, i.e. only proinsulin with the human sequence, is suitable for diabetes therapy (c.f., for example, German Pat. No. A1-3,232,036). Heterologous proinsulin has a significant immunogenicity. In this connection, it is remarkable that human proinsulins can also display variations in the C-peptide part.

Porcine insulin-Arg$^{B31}$OH and the corresponding diarginine derivative has only 62% and, respectively, 66% of the activity of unmodified porcine insulin, according to the investigations by Chance, Excerpta Medica International Congress Series No. 231, pages 292, 293.

Surprisingly, it has now been found that insulin-Arg$^{B31}$-OH, insulin-Arg$^{B31}$-Arg$^{B32}$-OH and other insulin derivatives in which the B chain carries a C-terminal organic group of basic character have, in contrast to proinsulin, a biological activity of approximately the same level as that of unmodified insulin.

The invention thus relates to medicaments for the treatment of diabetes mellitus consisting of a pharmaceutically acceptable carrier and an active compound, in which the active compound is an insulin derivative, with an isoelectric point between 5.8 and 8.5, of the formula I,
in which
$R^1$ denotes H or H-Phe,
$R^{30}$ represents the radical of a neutral L-aminoacid which can be genetically coded and
$R^{31}$ represents a physiologically acceptable organic group of basic character with up to 50 carbon atoms, in the build-up of which 0 to 3α-aminoacids participate and in which the optional terminal carboxyl group can be present in the free form, as an ester function, as an amide function, as a lactone or reduced to $CH_2OH$, or one of its physiologically acceptable salts.

The medicaments according to the invention are furthermore completely novel delayed action principles in which the action can be started without depot auxiliaries, such as zinc or protamine sulfate. The depot action is attributed to an inherent physical principle arising from protein chemistry, i.e. the sparing solubility of the insulin derivative at its isoelectric point. Redissolving of the derivative under physiological conditions is possibly achieved by splitting off the additional basic groups, which, depending on the derivative, is effected by tryptic or trypsin-like and/or carboxypeptidase B or carboxypeptidase B-like and/or esterase activity. The particular groups split off are either purely physiological metabolites, such as aminoacids, ornithine or choline, or physiologically acceptable substances which can easily be metabolized.

In contrast to the intermediates described in the literature, which still contain parts of the heterologous C-peptide, the insulin derivatives used as the active compounds of these novel medicaments also do not have a more powerful immunogenic effect than the corresponding insulin itself.

The abovementioned activity values of Chance, which are too low, possibly result from an inadequate purity of the fractions investigated or a systematic measurement error. In any case, their usefulness as active compounds in medicaments has not hitherto been known (perhaps because of this fact).

The agents according to the invention contain, as the active compound, one or more of the novel insulin derivatives of the formula I or insulin-Arg$^{B31}$-OH or insulin-Arg$^{B31}$-Arg$^{B32}$-OH.

They preferably have a pH value of between 2.5 and 8.5 and contain a suitable isotonicity agent, a suitable preservative and, if appropriate, a suitable buffer for a pH range between 5.0 and 8.5.

A typical use form of the derivatives described are products which, below the isoelectric point, are in the form of solutions in a physiologically acceptable excipient. The pH of the solution can be typically 5.0, i.e. is significantly higher than that of acid unmodified insulins (typically pH 3.0). In certain circumstances, a more neutral injection solution offers significant advantages in respect of tolerance.

Suspensions of amorphous or crystalline precipitates of the derivatives described in a physiologically acceptable excipient with about a neutral pH are another typical use form.

However, it is also possible to intensify the inherent sparing solubility in the derivatives in the physiological pH range by additional depot principles, such as, for example, by addition of zinc or protamine sulfate. The amount of zinc added can be up to 100 µg of $Zn^{2+}$/100 insulin units, typically about 50 µg of $Zn^{2+}$/100 insulin units. The amount of protamine can be between 0.28 mg and 0.6 mg per 100 units (based on protamine sulfate). In this manner, it is possible to prepare preparations having a particularly long action, for which there will in future be wider use than hitherto, since precisely a basal amount of insulin seems to be therapeutically advantageous. This has already been recognized from therapy with insulin metering units.

A suitable physiologically acceptable excipient medium which is compatible with the insulin derivative is a sterile aqueous solution which has been rendered isotonic with blood in the customary manner, for example by glycerol, sodium chloride or glucose, and which additionally also contains one of the usual preservatives, for example phenol, m-cresol or p-hydroxybenzoic acid esters. The excipient medium can additionally contain a buffer substance, for example sodium acetate, sodium citrate or sodium phosphate. Dilute acids (typically HCl) or alkalis (typically NaOH) are used to adjust the pH.

The insulin derivatives can also be used in the agents according to the invention in the form of alkali metal salts or ammonium salts. Any desired amount of one or more insulin derivatives of the formula I or an insulin derivative of the formula I can be mixed with other insulin derivatives of this type, in each case in the dissolved, amorphous and/or crystalline form, independently of one another.

It is sometimes advantageous to add to the formulation according to the invention a suitable amount of a suitable stabilizer which prevents precipitation of protein when the formulation is exposed to heat or mechanical stress on contact with various materials. Such stabilizers are known, for example, from European Pat. No. A-18,609, German Pat. No. A-3,240,177 or WO-83/00288.

In the agents according to the invention which can also contain suitable amounts of one of the known delayed action principles, such as, for example, protamine sulfate, globin or zinc, such a delayed action principle can be used in combination with the entire content of active compound or with parts thereof or one or more insulin derivatives of the formula I, in a mixture. An agent can contain various insulin derivatives of the formula I in combination with several different auxiliaries having a delaying action.

Diverse and very finely adjustable action characteristics can thus evidently be achieved with the therapeutic agents according to the invention; from the remarks made in the introduction, this should be associated with advances, especially in respect of delayed diabetic complications.

The following examples are intended to illustrate the invention further:

PREPARATION EXAMPLE 1

Human insulin-(B30)-O-$CH_2$-$CH_2$-$N^{\oplus}(CH_3)_3$ 5 g of porcine insulin are dissolved in 45 ml of dimethylformamide, 25 ml of dimethylsulfoxide, 0.5 ml of N-ethylmorpholine and 2.5 ml of water. 1.5 g of tert.-butoxycarbonyl-N-hydroxysuccinimide are added at room temperature, with stirring, and the mixture is allowed to react for 6 hours. The reaction is then stopped by addition of one drop of glacial acetic acid and the product is precipitated with either and filtered off. The residue is dissolved in 360 ml of dimethylformamide and the solution is diluted with 320 ml of tris buffer (0.05 M, 0.01M in $CaCl_2$, pH 7.5). Portions of 20 mg of trypsin are added at 36° C. at intervals of in each case 1 hour.

After a total of 12 additions, the pH is brought to 4.5 with acetic acid and the solution is evaporated. Subsequent purification of the material on a Sephadex ®-LH 20 column (8×200 cm) by means of partition chromatography in an n-butanol-glacial acetic acid-water (2:1:10) system gives 3.25 g of $N\alpha^{A1}$, $N\alpha^{B1}$-bis-Boc-des-$B_{23-30}$-octapeptide insulin (pig), which shows no further starting material in acid and basic electrophoresis. The aminoacid analysis of the substance is correct. After trial splitting off of the Boc groups, no further insulin activity is to be found. This material (3.25 g) is dissolved in 30 ml of dimethylformamide together with 100 mg of 1-hydroxybenzotriazole, 750 mg of HCl.Gly-Phe-Phe-Tyr(Bu$^t$)-Thr-Pro-Lys(Boc)-Thr(Bu$^t$)-O$CH_2CH_2$-$N^{\oplus}(CH_3)_3$.HCl and 0.5 ml of N-ethylmorpholine. 120 mg of dicyclohexylcarbodiimide are then added at room temperature and the reaction is stirred for 24 hours. The dicyclohexylurea precipitated is filtered off, and the product is precipitated by addition of either.

The precipitate is filtered off, washed with either and dried. The substance is prepurified by partition chromatography on Sephadex ®-LH 20 in the above system. 2.6 g of material from the main peak are isolated by precipitation with acetone/ether. The dried, still unprotected derivative is reacted with a mixture of 5 ml of trifluoroacetic acid and 1 ml of anisole at room temperature for 60 minutes. The crude substance is then precipitated from the solution, which is cooled with ice, by addition of either. The dried precipitate is dissolved in water and the product is precipitated with aqueous ammonia and centrifuged. The product is purified in 10% strength acetic acid over Sephadex ®-G 50 superfine or G 75. Human insulin-(B30)-OCH$_2$CH$_2$N$^\oplus$(CH$_3$)$_3$- can be isolated from the fractions of the desired peak by freeze-drying (yield after crystallization: 1.2 g). The insulin derivative thus obtained shows an activity equivalent to that of human insulin in a biological test.

The octapeptide of the formula III is prepared in accordance with the following condensation scheme by customary peptide condensation methods:

cation exchanger with 0.05M acetate, pH 4.0, using a sodium chloride gradient up to 0.5M. The appropriate fractions are combined and precipitated. After washing and recrystallization, 104 mg of porcine insulin-Arg$^{B31}$-Arg$^{B32}$-OH, which is identified by aminoacid analysis and characterized as uniform by HPLC and isoelectric focusing, are isolated.

The insulin derivative porcine insulin-Lys$^{B31}$-Arg$^{B32}$-OH is obtained in an analogous manner from the corresponding porcine proinsulin modified in position B31.

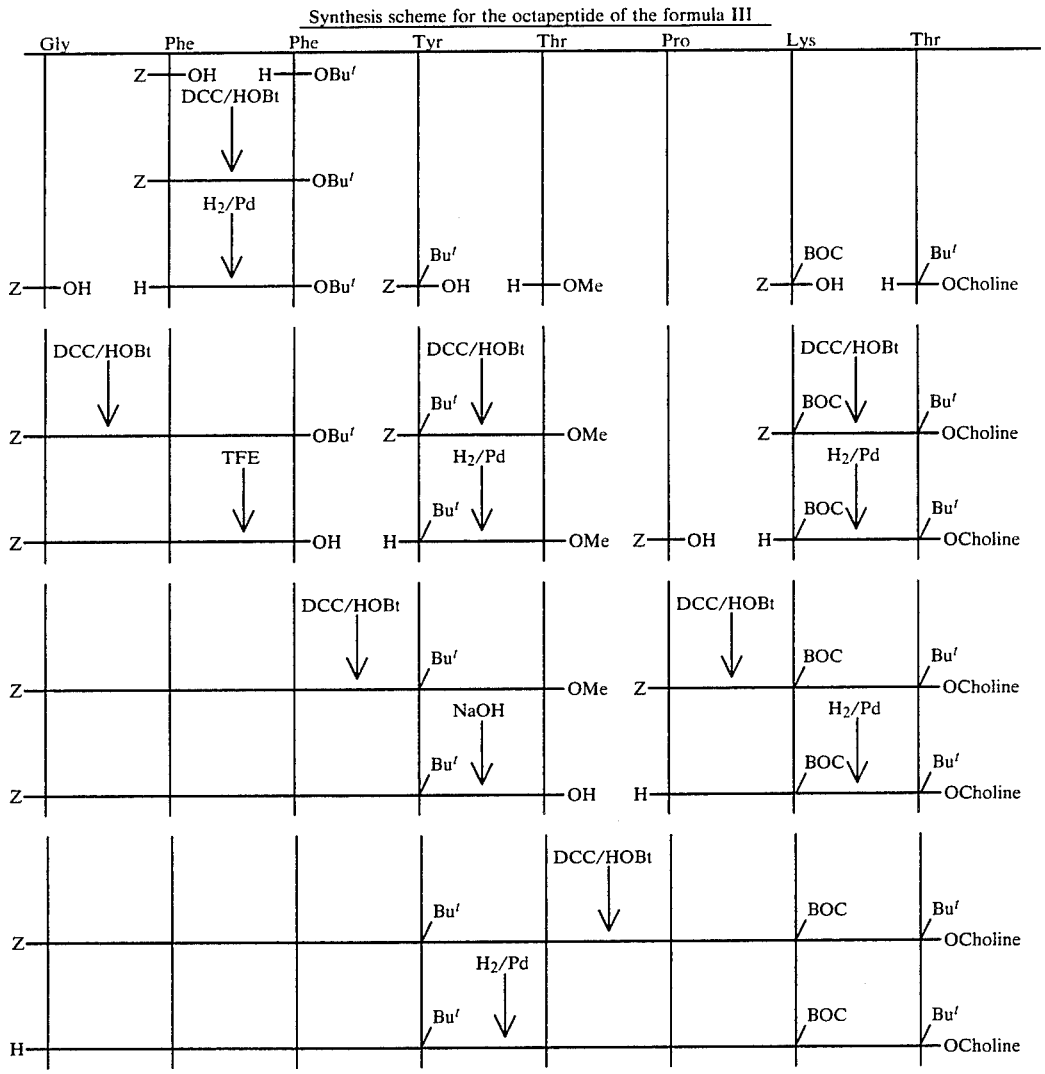

Synthesis scheme for the octapeptide of the formula III

The aminoacid and elemental analysis correspond to theory.

PREPARATION EXAMPLE 2

Porcine insulin-Arg$^{B31}$-Arg$^{B32}$-OH by tryptic digestion from porcine proinsulin 350 mg of porcine proinsulin are dissolved in 25 ml of 0.1M tris-HCl buffer, pH 7.5. 500 µg of trypsin are added to this solution at room temperature, turbidity occurring within a few hours. When the reaction has ended, the precipitate is centrifuged off, dissolved under acid conditions and analyzed with the aid of acetate film electrophoresis or HPLC. After renewed precipitation and washing of the precipitate, this is worked up in a manner which is known per se, or it is purified on a

MEDICAMENTS

EXAMPLE 1

Insulin-Arg$^{B31}$-Arg$^{B32}$-OH from pigs (prepared by tryptic digestion from proinsulin from pigs) in a weakly acid, dissolved formulation with 40 I.U. per ml and the depot activity thereof:

| | |
|---|---|
| Insulin—Arg$^{B31}$—Arg$^{B32}$—OH from pigs (27 I.U./mg) | 14.8 mg |
| Glucose (monohydrate), crystalline | 540.0 mg |
| Methyl p-hydroxybenzoate | 10.0 mg | are dissolved in a total volume of 10 ml of water. The pH value is brought to 4.5 by addition of 1N HCl or 1N NaOH.

Such solution shows a pronounced depot activity on rabbits in a dosage of 0.4 I.U./kg. The area under the blood sugar curve is the same as that of a standard product with 40 I.U./ml.

EXAMPLE 2

Human insulin-(B30)-choline ester, prepared by semi-synthesis from porcine insulin, in a neutral formulation with 40 I.U. per ml and the depot activity thereof:

| Human insulin-(B30)-choline ester (28 I.U./mg) | 14.3 mg |
| --- | --- |
| Sodium dihydrogen phosphate dihydrate | 21.0 mg |
| m-Cresol | 27.0 mg |
| Glycerol | 160.0 mg | are dissolved in a total volume of 10 ml of water. The pH vlaue is brought to 7.3 by addition of 1N HCl or 1N NaOH.

Such a suspension exhibits a marked depot activity on rabbits at a dosage of 0.4 I.U./kg.

EXAMPLE 3

Human insulin-Arg$^{B31}$-OH, prepared from porcine insulin by semi-synthesis, in the form of a crystalline NPH formulation with 40 I.U./ml and the severely delayed action thereof:

| Human insulin-Arg$^{B31}$—OH (27.5 I.U./mg) | 14.5 mg |
| --- | --- |
| Protamine sulfate | 1.3 mg |
| Sodium dihydrogen phosphate dihydrate | 21.0 mg |
| m-Cresol | 15.0 mg |
| Phenol | 6.0 mg |
| Glycerol | 160.0 mg | are dissolved in a total volume of 10 ml with water. The pH is brought to 7.3 by addition of 1N HCl or 1N NaOH.

Such a suspension of crystals exhibits a severely delayed action in rabbits at a dosage of 0.4 I.U./kg.

EXAMPLE 4

Mixture of human insulin-Arg$^{B31}$-OH and human insulin-Arg$^{B31}$-Arg$^{B32}$-OH, both prepared by semi-synthesis from porcine insulin, in the form of a zinc-containing suspension with 40 I.U./ml, and the severely delayed action thereof:

| Human insulin-Arg$^{B31}$—OH (27.5 I.U./mg) | 7.3 mg |
| --- | --- |
| Human insulin-Arg$^{B31}$—Arg$^{B32}$—OH (27.0 I.U./mg) | 7.4 mg |
| Zinc chloride (anhydrous) | 0.46 mg |
| Sodium acetate | 14.0 mg |
| Methyl p-hydroxybenzoate | 10.0 mg |
| Sodium chloride | 80 mg | are dissolved in a total volume of 10 ml with water. The pH value is brought to 7.0 by addition of 1N HCl or 1N NaOH.

Such a suspension exhibits a severely delayed action in rabbits at a dosage of 0.4 I.U./kg.

EXAMPLE 5

Human insulin-Arg$^{B31}$-Lys$^{B32}$-OCH$_3$, prepared by semi-synthesis from porcine insulin, in the form of a weakly acid, dissolved formulation with 100 I.U./ml, and the delayed action thereof:

| Human insulin-Arg$^{B31}$—Lys$^{B32}$—OCH$_3$ (27.0 I.U./mg) | 37.0 mg |
| --- | --- |
| Sodium acetate | 14.0 mg |
| Methyl p-hydroxybenzoate | 10.0 mg |
| Sodium chloride | 80.0 mg | are dissolved in a total volume of 10 ml with water. The pH is brought to 6.0 by addition of 1N HCl or 1N NaOH.

Such a solution exhibits a delayed action in rabbits.

EXAMPLE 6

Human insulin-Arg$^{B31}$-OH, prepared by tryptic splitting of primate preproinsulin of bacterial origin, in the form of NPH crystals, mixed with human insulin-Arg$^{B31}$-Arg$^{B32}$-OH, prepared by tryptic splitting from primate preproinsulin of bacterial origin:

| Human insulin-Arg$^{B31}$—OH (27.5 I.U./mg) | 11.1 mg |
| --- | --- |
| Human insulin-Arg$^{B31}$—Arg$^{B32}$—OH (27.0 I.U./mg) | 3.7 mg |
| Protamine sulfate | 1.0 mg |
| Sodium dihydrogen phosphate 2-hydrate | 21.0 mg |
| m-Cresol | 15.0 mg |
| Phenol | 6.0 mg |
| Glycerol | 160.0 mg | are dissolved in a total volume of 10 ml with water. The pH is brought to 7.2 by addition of 1N NaOH or 1N HCl.

This suspension exhibits a severely delayed action in rabbits (0.4 I.U./kg).

I claim:

1. An insulin derivative of the formula I

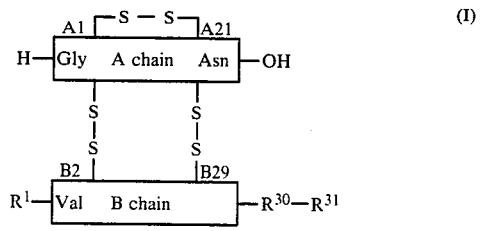

in which

R$^1$ denotes H or H-Phe

R$^{30}$ represents the radical of Ala, Thr or Ser and

R$^{31}$ represents a physiologically acceptable organic group of basic character of the formula X$_n$-S which has up to 50 carbon atoms, in which n is 0, 1, 2 or 3, X represents identical or different radicals of naturally occurring neutral or basic α-amino acids and S denotes OH or a physiologically acceptable group which blocks the carboxyl group but S being, if n is 0, a positively charged or protonatable basic radical or, if n is greater than 0, S can carry such a radical, or in which, if n is 2 or 3, the C-terminus X-S can also represent the homoserine lactone radical,
and which contains or does not contain a terminal carboxyl group or an ester or an amide thereof, and wherein, if $R^1$ represents H-Phe, the C-terminus —$R^{30}$—$R^{31}$ cannot denote —Thr(Arg)$_m$—OH, —Ala(Arg)$_m$—OH or —Ser—(Arg)$_m$—OH, where m is 1 or 2, which has an isoelectric point between 5.8 and 8.5, or a physiologically acceptable salt thereof.

2. An insulin derivative of the formula I as claimed in claim 1, in which (a)
$R^1$ denotes H and
$R^{31}$
(a 1) denotes a physiologically acceptable group $S^B$ which blocks the carboxyl group and carries a positively charged or protonatable basic radical,
(a 2.1) represents $X^N$—$S^B$, in which $X^N$ denotes the radical of a naturally occurring neutral L-aminoacid,
(a 2.2) represents $X^B$—S, in which $X^B$ denotes the radical of a naturally occurring basic L-aminoacid and S denotes OH or a group which blocks the carboxyl group and may or may not carry a positively charged or protonatable basic radical,
(a 3.1) represents —$X_n$—S, in which n is 2 or 3, X denotes the radicals $X^N$, $X^B$ or both and, if all the radicals X are $X^N$, S can denote only $S^B$,
(a 3.2) represents —$X_n$—Y, in which n is 1 or 2,
(a 3.3) represents —$X^B$—Z, —$X^B$—$X^N$—Z, —$X^N$—$X^B$—Z or $X^B$—$X^B$—Z, in which Z is Y or denotes the homoserine-lactone radical, or (b)
$R^1$ denotes H-Phe and
$R^{31}$
(b 1) is as defined under (a 1),
(b 2.1) is as defined under (a 2.1),
(b 2.2) denotes Lys—OH, Hyl—OH, Orn—OH, Cit—OH or His—OH,
(b 2.3) represents $X^B$—S′, in which S′ has the meaning of S, with the exception of OH,
(b 3.1) represents X—X′—OH or —X′—X—OH, in which X′ is as defined under (b 2.2),
(b 3.2) represents X$_2$—S′,
(b 3.3) is as defined under (a 3.1), in which n is 3,
(b 3.4) is as defined under (a 3.2) or (a 3.3), or a physiologically acceptable salt thereof.

3. A pharmaceutical composition comprising an effective amount of an insulin derivative, with an isoelectric point between 5.8 and 8.5, of the formula I,

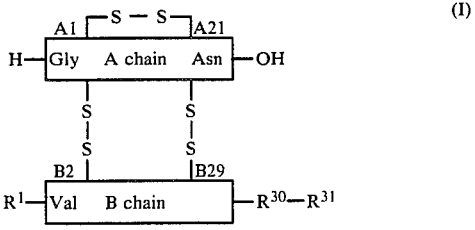

in which
$R^1$ denotes H or H—Phe
$R^{30}$ represents the radical of Ala, Thr or Ser and
$R^{31}$ represents a physiologically acceptable organic group of basic character of the formula $X_n$—S which has up to 50 carbon atoms, in which
n is 0, 1, 2 or 3,
X represents identical or different radicals of naturally occurring neutral or basic α-amino acids and
S denotes OH or a physiologically acceptable group which blocks the carboxyl group but S being, if n is 0, a positively charged or protonatable basic radical or, if n is greater than 0, S can carry such a radical, or in which, if n is 2 or 3, the C-terminus X-S can also represent the homoserine lactone radical,
and which contains or does not contain a terminal carboxyl group or an ester or an amide thereof, or one of its physiologically acceptable salts.

4. A pharmaceutical composition comprising an effective amount of an insulin derivative, with an isoelectric point between 5.8 and 8.5, of the formula I.

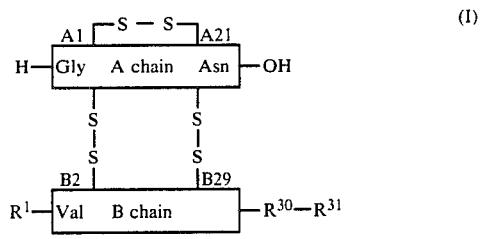

in which
$R^1$ denotes H or H—Phe
$R^{30}$ represents the radical of Ala, Thr or Ser and
$R^{31}$ represents —Arg—OH or —Arg—Arg—OH or an ester or an amide thereof, or one of its physiologically acceptable salts.

5. A method of treating a patient suffering from diabetes mellitus which comprises administering an effective amount of a composition according to claim 3 or a pharmaceutically acceptable salt thereof.

6. A pharmaceutical composition as claimed in claim 4, wherein $R^{31}$ represents —Arg—OH.

7. A composition as claimed in claim 4, wherein $R^{31}$ represents —Arg—Arg—OH.

8. An insulin derivative of claimed in claim 1, in which $R^1$ represents H—Phe.

9. An insulin derivative as claimed in claim 1, in which the A chain and the (B2-29) chain have the sequence of human insulin.

10. An insulin derivative as claimed in claim 2, in which the aminoacid radicals X, $X^N$ and $X^B$ and the radicals Y and Z are in the L-configuration.

11. An insulin derivative as claimed in claim 2, in which S or S′ represents (C$_1$ to C$_6$)-alkoxy, (C$_3$ to C$_6$)-cycloalkoxy, NH$_2$, (C$_1$ to C$_6$)-alkylamino, di-(C$_1$ to C$_6$)-alkylamino, amino-(C$_2$ to C$_6$)-alkoxy, (C$_1$ to C$_4$)-alkylamino-(C$_2$ to C$_6$)-alkoxy, di-(C$_1$ to C$_4$)-alkylamino-(C$_2$ to C$_6$)-alkoxy, tri-(C$_1$ to C$_4$)-ammonio-(C$_2$ to C$_6$)-alkoxy, amino-(C$_2$ to C$_6$)-alkylamino, [(C$_1$ to C$_4$)-alkylamino]-(C$_2$ to C$_6$)-alkylamino, [di-(C$_1$ to C$_4$)-alkylamino]-(C$_2$ to C$_6$)-alkylamino or [tri-(C$_1$ to C$_4$)-alkylammonio]-(C$_2$ to C$_6$)-alkylamino and $S^B$ has one of the last eight meanings mentioned.

12. A pharmaceutical composition comprising an effective amount of an insulin derivative or a mixture of compounds according to claim 1 or a pharmaceutically acceptable salt thereof and a pharmaceutically acceptable carrier.

13. An agnet as claimed in claim 3, which has a pH value between 2.5 and 8.5 and contains a suitable isotonicity agent and a suitable preservative and in which the insulin derivative of the formula I is in dissolved form or in suspension or a combination thereof.

14. An agent as claimed in claim 3, which contains a suitable buffer and has a pH value between 4.0 and 8.5.

15. An agent as claimed in claim 3, which contains between 0 and 100 μg of zinc/100 I.U.

16. An agent as claimed in claim 3, in which the insulin derivative of the formula I is in the form of an alkali metal salt or the ammonium salt.

17. An agent as claimed in claim 3, in which any desired amount of one or more insulin derivatives of the formula I is mixed with other insulin derivatives of this type in dissolved, amorphous or crystalline form or in a combination thereof in each case, independently of one another.

18. An agent as claimed in claim 3, which contains a suitable amount of an auxiliary having a delaying action.

19. An agent as claimed in claim 18, in which this delayed action principle is used in combination with the entire content of active compound or with parts thereof or one or more insulin derivatives of the formula I, in a mixture.

20. An agent as claimed in claim 3, which contains various insulin derivatives of the formula I in combination with at least two different auxiliaries having a delaying action.

21. An insulin derivative of the formula I

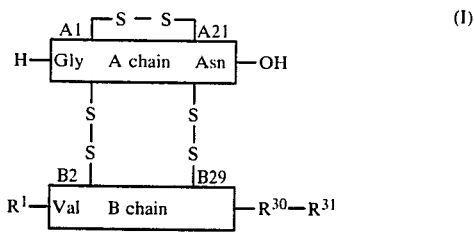

in which
$R^1$ denotes H or H-Phe,
$R^{30}$ represents the radical of Ala, Thr or Ser and
$R^{31}$ represents a physiologically acceptable organic group of basic character of the formula $X_n$-S which has up to 50 carbon atoms, in which
n is 0, 1, 2 or 3,
X represents identical or different radicals of naturally occurring neutral or basic α amino acids and
S denotes OH or a physiologically acceptable group which blocks the carboxyl group but S being, if n is 0, a positively charged or protonatable basic radical or, if n is greater than 0, S can carry such a radical, or in which, if n is 2 or 3, the C-terminus X-S can also represent the homoserine lactone radical,
and the terminal group is a carboxyl group or an ester or an amide thereof, and wherein, if $R^1$ represents H-Phe, the C-terminus $-R^{30}-R^{31}$ cannot denote -Thr(Arg)$_m$OH, -Ala(Arg)$_m$OH or -Ser(Arg)$_m$OH, where m is 1 or 2, or ThrR$^{31}$ in which R$^{31}$ is (a) an amino acid, (b) a peptide or (c) an amide or ester of (a) or (b),
which has an isoelectric point between 5.8 and 8.5, or a physiologically acceptable salt thereof.

* * * * *